United States Patent
Cole et al.

(10) Patent No.: US 10,561,818 B2
(45) Date of Patent: Feb. 18, 2020

(54) PRE-CURVED STEERABLE CATHETER WITH PULL-WIRES FOR DEXTEROUS DEFLECTION CONTROL

(71) Applicants: KONINKLIJKE PHILIPS N.V., Eindhoven (NL); THE JOHNS HOPKINS UNIVERSITY, Baltimore, MD (US)

(72) Inventors: Gregory Cole, Ossining, NY (US); Hao Su, Hartsdale, NY (US); Vijay Parthasarathy, Lexington, MA (US); Rex Yung, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 101 days.

(21) Appl. No.: 15/529,574

(22) PCT Filed: Nov. 20, 2015

(86) PCT No.: PCT/IB2015/059000
§ 371 (c)(1),
(2) Date: May 25, 2017

(87) PCT Pub. No.: WO2016/087978
PCT Pub. Date: Jun. 9, 2016

(65) Prior Publication Data
US 2017/0368304 A1    Dec. 28, 2017

Related U.S. Application Data

(60) Provisional application No. 62/085,702, filed on Dec. 1, 2014.

(51) Int. Cl.
*A61M 25/00* (2006.01)
*A61M 25/01* (2006.01)

(52) U.S. Cl.
CPC .... *A61M 25/0041* (2013.01); *A61M 25/0147* (2013.01); *A61M 25/0152* (2013.01); *A61M 2025/0161* (2013.01)

(58) Field of Classification Search
CPC .......... A61M 25/0041; A61M 25/0147; A61M 2025/0161; A61M 25/0152; A61M 25/0136
See application file for complete search history.

(56) References Cited

U.S. PATENT DOCUMENTS

| | | |
|---|---|---|
| 5,282,479 A | 2/1994 | Havran |
| 6,458,107 B1 | 10/2002 | Ockuly |
| 2003/0181855 A1 | 9/2003 | Simpson et al. |
| 2004/0039371 A1 | 2/2004 | Tockman et al. |
| 2005/0075661 A1 | 4/2005 | Levine et al. |

(Continued)

FOREIGN PATENT DOCUMENTS

JP    02283347 A    11/1990

*Primary Examiner* — Emily L Schmidt

(57) ABSTRACT

A pre-curved steerable catheter includes a catheter body (102) having a distal end portion. The distal end portion includes a permanently curved flexible end portion (110). A pull wire (108) is disposed in a pull wire lumen within the catheter body. The pull wire extends from the distal end portion to a proximal end portion of the catheter body wherein the pull wire, when tensioned, provides a change in an angle of the curved flexible end portion of the catheter body.

9 Claims, 4 Drawing Sheets

(56) References Cited

U.S. PATENT DOCUMENTS

| | | |
|---|---|---|
| 2006/0064056 A1 | 3/2006 | Coyle et al. |
| 2007/0156114 A1* | 7/2007 | Worley ............... A61B 18/1492 604/525 |
| 2007/0270579 A1 | 11/2007 | Jadhav et al. |
| 2008/0255475 A1 | 10/2008 | Kondrosky et al. |
| 2009/0156995 A1 | 6/2009 | Martin et al. |
| 2009/0306545 A1 | 12/2009 | Elsakka et al. |
| 2011/0082810 A1 | 4/2011 | Holtz-Davis et al. |
| 2011/0270229 A1 | 11/2011 | Tanaka et al. |
| 2012/0143088 A1* | 6/2012 | Schultz ................ A61B 5/6852 600/585 |
| 2012/0158021 A1 | 6/2012 | Morrill |
| 2012/0203142 A1 | 8/2012 | Bedell |
| 2014/0276612 A1 | 9/2014 | Sevensma |

* cited by examiner

PRE-CURVED STEERABLE CATHETER WITH PULL-WIRES FOR DEXTEROUS DEFLECTION CONTROL

CROSS-REFERENCE TO PRIOR APPLICATIONS

This application is the U.S. National Phase application under 35 U.S.C. § 371 of International Application Serial No. PCT/IB2015/059000, filed on Nov. 20, 2015, which claims the benefit of U.S. Application Ser. No. 62/085,702, filed on Dec. 1, 2014. These applications are hereby incorporated by reference herein.

BACKGROUND

Technical Field

This disclosure relates to medical instruments and more particularly to catheter devices having a pre-curved tip that includes a curvature adjustment capability.

Description of the Related Art

Pull-wire steerable catheters and pre-curved navigation catheters can be employed to successfully navigate to a variety of target locations. However, these designs have their drawbacks.

Pre-curved catheters are very simple to navigate. A user inserts and rotates the catheter to point the pre-curved portion into a lumen. The user does not need to actuate the catheter end portion in any way. This allows a fairly simple one handed operation. For example, when the catheter reaches a bifurcation, the catheter is rotated until the curved tip is pointing to a desired pathway, and then the catheter is advanced further into the pathway.

The static nature of the tool can lead to difficulties. Pre-curved catheters generally come in sets with different curve angles, and the most appropriate curve angle must be selected to achieve a successful navigation. Since there is no way to change the shape of the catheter during navigation, more than one catheter often must be used to achieve all of the desired target locations. In a peripheral lung navigation example, when there are a variety of different curve angles and airway diameters on a given trajectory, a pre-curved catheter often cannot reach the desired target location.

Pull wire catheters are generally straight tipped or uncurved, but have a lumen with a pull wire. The catheter bends when the pull-wire is retracted. The longer it retracts, the more it bends, generating a smaller diameter arch. This kind of catheter has difficulties from a positioning perspective. Some of these difficulties include the following. To achieve the steering capability, the pull wire catheter requires a relatively large space to extend its shaft to achieve the desired approaching angle. This makes it difficult to orient the catheter toward small targets or bifurcations. The operator must be able to dexterously interact with control knobs on the handle of the catheter, as well advance and rotate the catheter, making single operator use quite awkward.

Tracking the direction of pull wire steering can be difficult. When the catheter is inserted through a tortuous path, the orientation of the tip with respect to the handle is not easily known. This can lead to frustration during navigation as the clinician does not know which direction the tip will move when actuated.

SUMMARY

In accordance with the present principles, a pre-curved steerable catheter includes a catheter body having a distal end portion, the distal end portion including a permanently curved flexible end portion. At least one pull wire is disposed in a pull wire lumen within the catheter body. The at least one pull wire extending from the distal end portion to a proximal end portion of the catheter body wherein the at least one pull wire, when tensioned, provides a change in an angle of the curved flexible end portion of the catheter body.

Another pre-curved steerable catheter includes a catheter body having a distal end portion, the distal end portion including a permanently curved flexible end portion. At least one pull wire is disposed in a pull wire lumen within the catheter body, the at least one pull wire extending from the distal end portion to a proximal end portion of the catheter body. A handle is configured to tension the at least one pull wire and provide a change in an angle of the curved flexible end portion of the catheter body.

Yet another pre-curved steerable catheter includes a catheter body having a distal end portion, the distal end portion including a permanently curved flexible end portion. The curved flexible end portion includes a relaxed position having a first curved angle extending outwardly from a longitudinal axis of the catheter body. A plurality of pull wires is disposed in one or more pull wire lumens within the catheter body and extend longitudinally along the catheter body. A first pull wire is disposed on an inside curve of the catheter body, and a second pull wire is disposed on an outside curve of the catheter body such that tensioning the first pull wire results in the angle being steeper than the first curved angle and tensioning the second pull wire results in the angle being one of shallower than the first curved angle or extending past the longitudinal axis in an opposite direction from the first curved angle. A handle is configured to tension the at least one pull wire and provide a change in an angle of the curved flexible end portion of the catheter body.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1B:
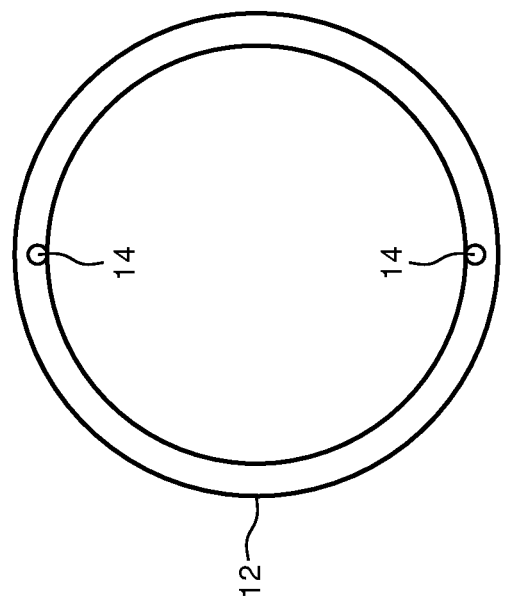
FIG. 1B is a cross-sectional view taken at section line 1B-1B of FIG. 1A showing two pull wires in a catheter body in accordance with one embodiment.

In accordance with the present principles, a steerable catheter is provided which utilizes a pre-curved tip in a default position for navigation and includes at least one pull wire to permit a clinician to dynamically change the angle of the pre-curved catheter. By permitting the clinician to adjust the angle of the curvature of a pre-curved catheter, the ease of use of a pre-curved catheter is maintained, and the versatility of a steerable pull wire is also provided. This creates a versatile and easy to use navigation catheter.

Navigation through the airways of the lungs is a complicated undertaking due to the varying diameters of airways and changing angles of bifurcations. The pre-curved pull-wire catheter may include one or more pull wires to allow the clinician to operate the catheter as a pre-curved device, but when faced with a turn that cannot be passed with the pre-curve angle alone, the pre-curved pull-wire catheter permits the catheter tip to be actuated by the pull wire to change the steering angle. In one embodiment the steering angle is increased, and, in another embodiment, decreased. This provides simplistic and quick operation of a pre-curved catheter, but with the versatility of a pull-wire steerable catheter.

The pre-curved pull-wire catheter in accordance with the present principles is a steerable catheter that can be employed as a navigation vehicle to deliver diagnostic or therapeutic tools. One major difficulty to be solved is the creation of a versatile tool that is easy for a clinician to use in navigating to all sites within the human anatomy, ranging from lung airway to blood or other vessels, etc. The catheter in accordance with the present principles may be employed not only for navigation, but applied to a broad range of interventional procedures that need dexterous navigation inside an anatomical structure, including but not limited to a heart, a vasculature, a liver, a kidney, a uterus, a urethra, etc.

It should be understood that the present invention will be described in terms of medical instruments; however, the teachings of the present invention are much broader and are applicable to any elongated instruments. In some embodiments, the present principles are employed in tracking or analyzing complex biological or mechanical systems. In particular, the present principles are applicable to internal procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware. It should be noted that the control and navigation of devices in accordance with the present principles may include the use of hardware capable of executing software in association with appropriate software.

All statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the diagrams presented herein represent conceptual views of illustrative system components embodying the principles of the invention. Similarly, it will be appreciated that any diagrams and the like represent various processes which may be substantially represented in computer readable storage media and so executed by a computer or processor, whether or not such computer or processor is explicitly shown.

Figure 1A:
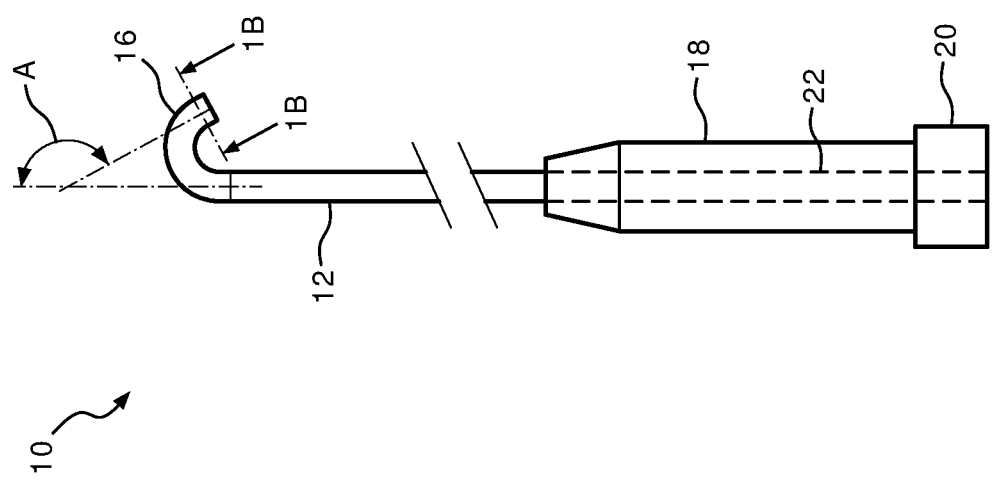
FIG. 1A is a side view of a pre-curved steerable catheter system in accordance with the present principles.

Referring now to the drawings in which like numerals represent the same or similar elements and initially to FIGS. 1A and 1B, a perspective view of an illustrative pre-curved steerable catheter system 10 is shown in accordance with one embodiment. The catheter system 10 includes a catheter body 12 having a pre-curved end portion 16. The catheter body 12 may include any suitable flexible material, such as polyurethane or other plastic material. The pre-curved end portion 16 may include an angle or arc that forms an angle "A" of between about 60 degrees (or less) to about 170 degrees (or more), optimally selected for the targeted navigation pathway.

In one embodiment, the catheter body 12 supports pull wires 14 therein. While the pull wires 14 are preferably provided internally to the catheter 12, in some embodiments the pull wires may be disposed externally to the catheter 12. While two pull wires 14 are depicted in FIG. 1B, the catheter body 12 may include a single pull wire or two or more pull wires, as needed. The pull wire(s) 14 may be disposed in a separate lumen in the catheter wall. The pre-curved portion 16 of the catheter 12 can be adjusted with the pull wire 14 within a pull-wire lumen to add additional curvature to the pre-curved portion 16 of the catheter body 12, or lessen the curvature in pre-curved portion 16 of the catheter 12. It should be noted that pre-curved refers to a permanent curvature that may be manufactured into a distal end portion of the catheter 12.

The catheter system 10 includes a handle 18 to attach to a catheter shaft to allow a clinician to easily maneuver the catheter body 12, while still permitting the clinician to adjust the curve angle. An adjustment mechanism 20 may be disposed on the handle 18 to permit the user to easily make adjustments to the catheter angle. The adjustment mechanism 20 and the handle 18 permit access to a catheter body lumen 22 from a proximal end of the handle 18 and adjustment mechanism 20. The adjustment mechanism 20 may include a tensioning mechanism and a lock to hold pull wire tension and therefore a catheter body configuration, during a procedure or the like.

Figure 2:
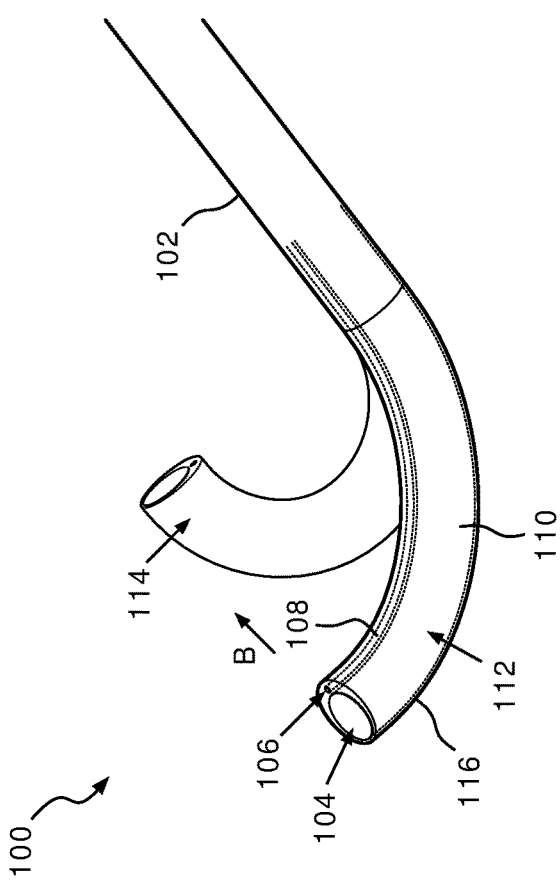
FIG. 2 is a perspective view of a pre-curved steerable catheter having a pull wire on an inside curve of the catheter body in accordance with one embodiment.

Referring to FIG. 2, a diagram shows a relaxed position and deflected position of a pre-curved steerable catheter 100 in accordance with one illustrative embodiment. The catheter 100 includes a catheter body 102 that forms a catheter lumen 104. A wall of the catheter body 102 forms a pull wire lumen 106. A pull wire 108 is operatively disposed within the pull wire lumen 106. The catheter body 102 is pre-curved and includes an arced end portion 110. The arced end portion 110 includes a permanently curved flexible end portion. The arced end portion 110 is provided within the memory of the material forming the catheter body 102. Since the catheter body 102 includes a flexible material, when the pull wire is activated from a relaxed position 112, the pre-curve becomes more severe as indicated by a deflected position 114.

In one embodiment, the catheter body 102 includes several segments of different rigidity along a length of the catheter body 102 such that when force is applied to the pull-wire 108, a distal tip of the catheter deflects to a much larger degree than proximal sections due to the lower rigidity. Hence, a semicircular-like arc shape may be achieved. The segments of different rigidity may include segments of varying thickness, varying material, nested segments, inserts within the material matrix of the catheter body 102, etc.

In the case shown in FIG. 2, the pre-curve is in a same direction "B" of the pull wire motion, allowing for greater deflection. When a catheter tip 116 is pre-curved in the same direction as the pull-wire deflection, it can be curved to any angle (about 180 degrees for an angle "A"). This permits articulation of the catheter pull wire 108 to enable the catheter body 102 to achieve different approaching angles.

Figure 3:
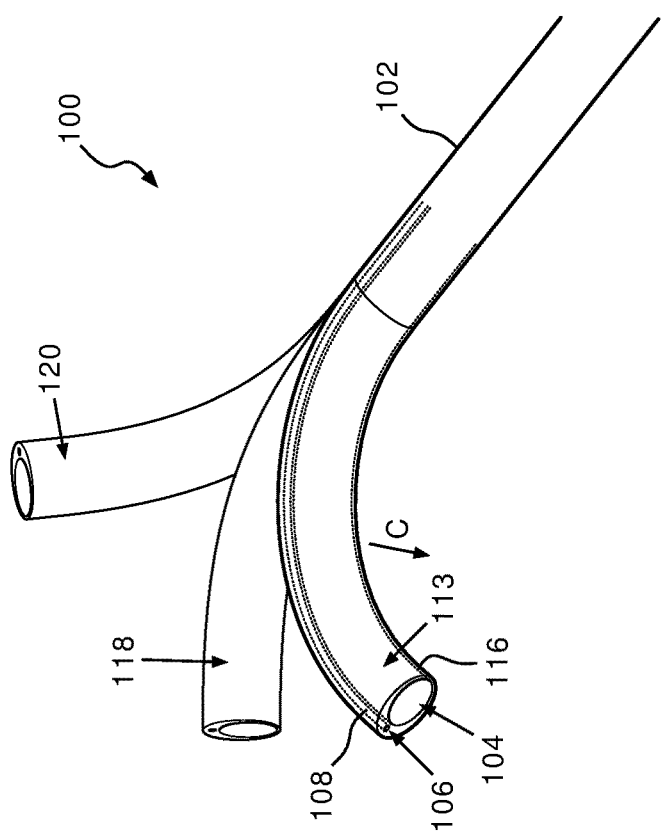
FIG. 3 is a perspective view of a pre-curved steerable catheter having a pull wire on an outside curve of the catheter body in accordance with another embodiment.

Referring to FIG. 3, a diagram shows a relaxed position and deflected positions of the pre-curved steerable catheter 100 in accordance with one illustrative embodiment. In the case shown in FIG. 3, the catheter body 102 is pre-curved in direction "C", which is opposite the direction of pull-wire deflection. The pre-curve includes a relaxed position 113. The pre-curve opposite the pull wire motion permits for straightening (position 118) and eventually curving the catheter body 102 in an opposite direction (position 120). The catheter body 102 may be pre-curved to the extreme end of clinically useful catheter angles, such as 160-190 degrees. This permits actuation of the pull-wire 108 to first "straighten" a catheter tip or end portion 116 to position 118, and them permit curving all the way out to other therapeutically useful curvature angles (illustratively shown at position 120).

In accordance with another embodiment, the catheter body 102 may also include a pull wire on both sides (e.g., embed two pull wires 108) so that the tip can be deflected in both directions, e.g., a combination of FIGS. 2 and 3 pull wire configurations (see FIG. 1). Each of the catheter bodies are preferably interfaced with a handle. Two handle embodiments will be illustratively described herein.

Figure 4:
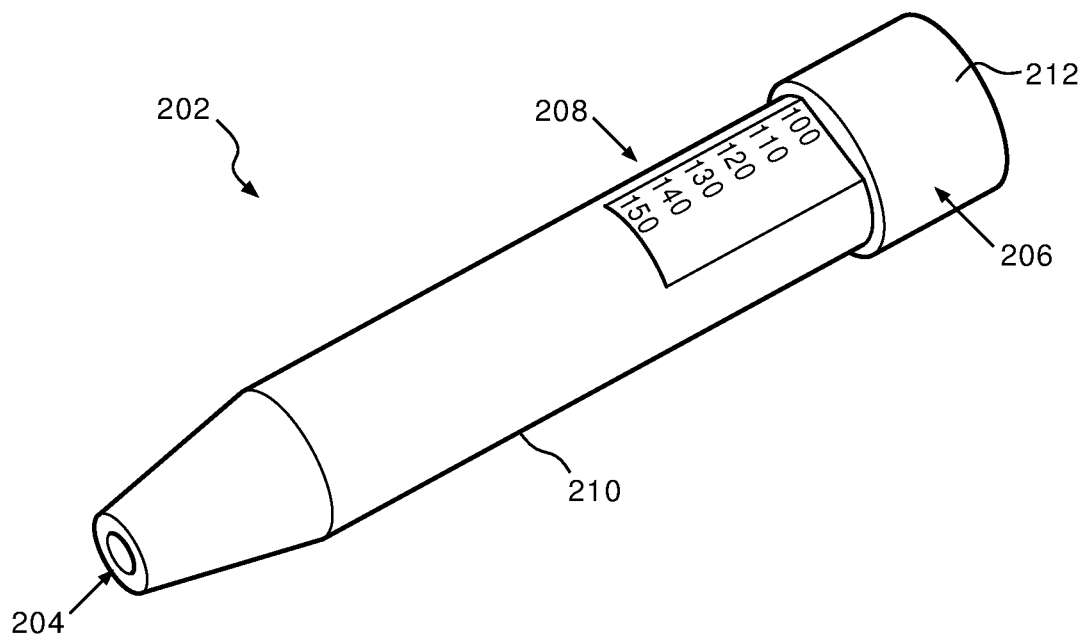
FIG. 4 is a perspective view of a catheter handle for tensioning and locking a pull wire in accordance with one embodiment.

Referring to FIG. 4, a perspective view of a handle 202 is shown for preset catheter curve workflow in accordance with the present principles. The handle 202 includes a main body 210 that forms a mounting or attachment point 204 for the catheter body (102). The main body 210 of the handle 202 may include any useful shape. The main body 210 includes a lumen for receiving a catheter body with a passthrough opening (not shown) for access to the tool lumen (104) of the catheter on a proximal end of the handle 202. The handle 202 includes a pull-wire tensioner/pull slide 206. The pull slide 206 allows the user to unlock a tip angle, adjust the curvature position of the tip, then relock the tip angle adjustment. The pull slide 206 may be rotatable or include a rotatable portion (e.g., a rotatable cap 212) to tighten or loosen the pull-slide 206.

An indicator 208 shows the tip angle for the amount of curvature imparted to the tip of the catheter body (102). The handle 202 supports a similar workflow to that of a conventional pre-curved catheter. The pull slide 206 is associated with a position on the indicator 208. The pull slide/pull-wire tensioner 206 may include the rotatable cap 212 that can be locked in place to maintain the tip angle. Because the tip adjustment is locked into place, a compliant mechanism to allow the catheter tip to deflect may be needed so that the tip can move naturally. This compliance may be provided within the handle 202 or within the pull wire.

Figure 5:
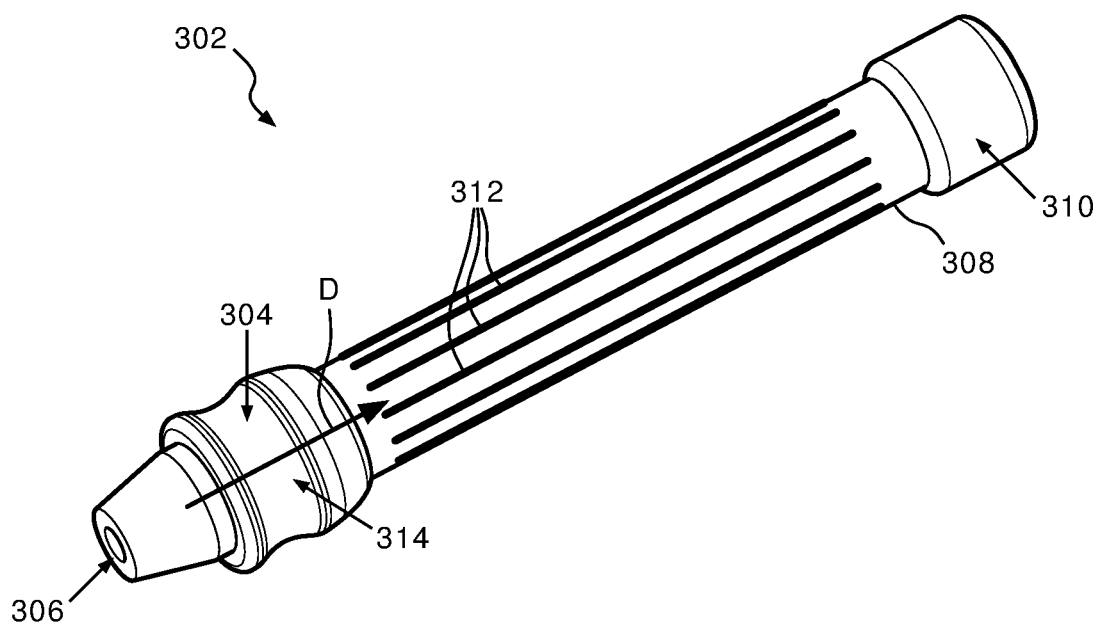
FIG. 5 is a perspective view of a catheter handle for tensioning and locking a pull wire, the handle having a circumferential spring-loaded pull slide in accordance with another embodiment.

Referring to FIG. 5, a perspective view of a handle 302 is shown for preset catheter curve workflow in accordance with the present principles. The handle 302 includes a main body 308 that forms a mounting or attachment point 306 for the catheter body (102). The main body 308 of the handle 302 may include any shape. In the embodiment shown, the main body includes grip ridges 312. A circumferential pull slide 304 is configured to actuate a pull wire in the direction of arrow "D", the slide 304 includes a rotating locking portion 314 that can be rotated to lock and release the pull slide 304. The pull slide 304 provides tip deflection adjustment. Note the circumferential slide 304 ensures ease of actuation regardless of handle angle and includes a spring return (not shown) encased in the handle 302.

A passthrough (not shown) through a rear pommel 310 is provided for the central lumen of the catheter body. The grips 312 and rear pommel 310 increase security in the hand while rotating and actuating the pull slide 304.

Handle 302 provides for a dynamic curvature adjustment workflow. A clinician is constantly in control of the catheter tip curve angle. The handle 302 provides a triggering mechanism that the clinician can actuate with their finger and includes a spring return. The spring return ensures that the clinician only has to apply force in one direction on the triggering mechanism (304) making it simpler to operate, and when the clinician is not interacting with the trigger, the catheter tip angle is in a known and stable state. Due to the desired operation of steering by rotation, the actuation interface (304) (circumferential pull-slide 304) is independent of the angular position of the catheter, since the pull wire slide 304 is circumferential and symmetric around the body 308 of the catheter. In this way, the clinician can deflect the tip just as easily from any state of longitudinal rotation.

Applications in accordance with the present principles involve catheter based bronchoscope or endoscope procedures that need precise positioning of interventional instruments, which are extended out of the catheter for tissue manipulations. The present embodiments have broad impact on any application scenarios where either pre-curved steerable catheters or pull-wire steerable catheters are being used clinically.

Figure 6:
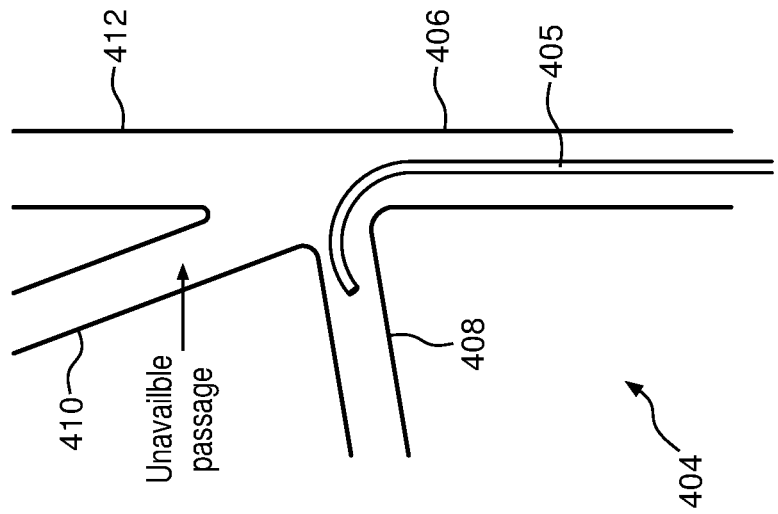
FIG. 6 is a diagram showing the usage of a pre-curved steerable catheter in accordance with one example.
Figure 6:
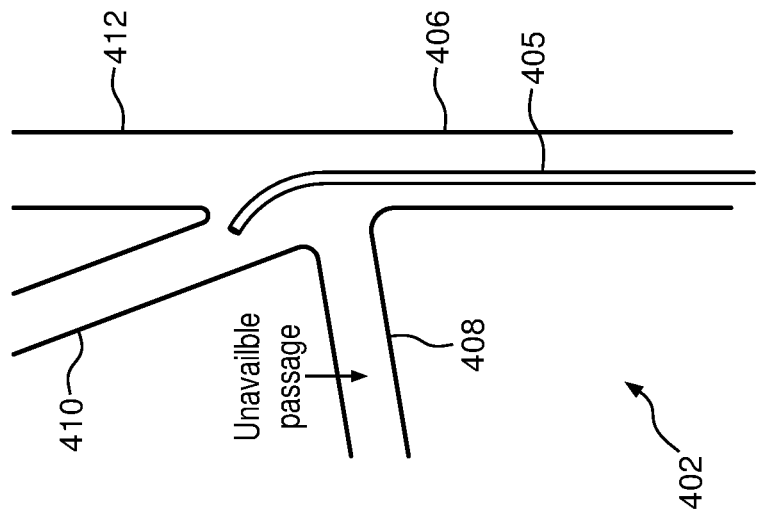

Referring to FIG. 6, a diagram shows two instances for catheter use in an interventional procedure. In a first instance 402, a pre-curved steerable catheter 405 in accordance with the present principles is advanced down a passage 406. The passage 406 includes a plurality of bifurcations 408, 410 and 412, each having a different angular relationship with passage 406. Some passages (410, 412) can be navigated using the precurved aspect of the catheter alone. In the present embodiment, the catheter 405 includes a permanent 60 degree precurve. A target along a bifurcated passage 408 would be too difficult or impossible to navigate relying solely on the precurved catheter 405.

Catheter 405 includes a steerable component as shown in instance 404. The catheter 405 is tensioned using a pull wire (not shown) to increase the precurve to 130 degrees. With the 130 degrees adjustment, the catheter 405 is steerable into the passage 408 in accordance with the present principles. In this way, the need for multiple catheters is avoided and access is provided to an otherwise unavailable passage.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for a pre-curved steerable catheter with pull-wires for dexterous deflection control (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A pre-curved steerable catheter, comprising:
   a catheter body having a distal end portion, the distal end portion including a permanently curved flexible end portion;
   at least one pull wire disposed in a pull wire lumen within the catheter body, the at least one pull wire extending from the distal end portion to a proximal end portion of the catheter body; and
   a handle configured to adjust the at least one pull wire with a slide,
   wherein the slide includes a lock to lock an angle at an indicated position displayed on an indicator on the handle;
   wherein the at least one pull wire, when tensioned, provides a change in the angle of the curved flexible end portion of the catheter, and
   wherein the handle is configured to adjust the at least one pull wire with a spring loaded circumferential slide.

2. The catheter as recited in claim 1, wherein the curved flexible end portion includes a relaxed position having a first curved angle extending outwardly from a longitudinal axis of the catheter body and the at least one pull wire is a single pull wire disposed on an inside curve of the catheter body.

3. The catheter as recited in claim 2, wherein the curved flexible end portion includes segments of varied rigidity such that the single pull wire, when tensioned, results in a second curved angle steeper than the first curved angle.

4. The catheter as recited in claim 1, wherein the curved flexible end portion includes a relaxed position having a first curved angle extending outwardly from a longitudinal axis of the catheter body and the at least one pull wire is only a single pull wire disposed on an outside curve of the catheter body.

5. The catheter as recited in claim 4, wherein the single pull wire, when tensioned, results in a second curved angle which is one of shallower than the first curved angle or extends past the longitudinal axis in an opposite direction of the first curved angle.

6. The catheter as recited in claim 1, wherein the at least one pull wire includes two pull wires, a first pull wire is disposed on an inside curve of the catheter body and a second pull wire is disposed on an outside curve of the catheter body.

7. A pre-curved steerable catheter, comprising:
   a catheter body having a distal end portion, the distal end portion including a permanently curved flexible end portion;
   at least one pull wire disposed in a pull wire lumen within the catheter body, the at least one pull wire extending from the distal end portion to a proximal end portion of the catheter body; and
   a handle configured to tension the at least one pull wire with a slide and provide a change in an angle of the curved flexible end portion of the catheter body wherein the slide includes a lock to lock the angle at an indicated position,
   wherein the handle is configured to adjust the at least one pull wire with a spring loaded circumferential slide.

8. A pre-curved steerable catheter, comprising:
   a catheter body having a distal end portion, the distal end portion including a permanently curved flexible end portion, the curved flexible end portion includes a relaxed position having a first curved angle extending outwardly from a longitudinal axis of the catheter body;
   a plurality of pull wires disposed in one or more pull wire lumens within the catheter body and extending longitudinally along the catheter body, a first pull wire being disposed on an inside curve of the catheter body and a second pull wire being disposed on an outside curve of the catheter body such that tensioning the first pull wire results in the angle being steeper than the first curved angle and tensioning the second pull wire results in the angle being one of shallower than the first curved angle or extending past the longitudinal axis in an opposite direction from the first curved angle; and
   a handle configured to adjust at least one pull wire with a spring loaded circumferential slide and provide a change in an angle of the curved flexible end portion of the catheter body wherein the slide includes a lock to lock the angle at an indicated position displayed on an indicator on the handle.

9. The catheter as recited in claim 8, wherein the permanently curved flexible end portion includes segments of varied rigidity such that the at least one pull wire, when tensioned, results in the angle being steeper than the first carved angle.

* * * * *